United States Patent
Haesler et al.

(10) Patent No.: US 11,931,160 B2
(45) Date of Patent: Mar. 19, 2024

(54) BRAIN INTERACTION APPARATUS, CRANIAL ANCHOR, AND RELATED SYSTEMS AND METHODS

(71) Applicants: IMEC VZW, Leuven (BE); Katholieke Universiteit Leuven, KU LEUVEN R&D, Leuven (BE); VIB, Ghent (BE)

(72) Inventors: Sebastian Haesler, Leuven (BE); Luis Diego Leon Hoffman, Leuven (BE)

(73) Assignees: Imec vzw, Leuven (BE); Katholieke Universiteit Leuven, Leuven (BE); VIB, Ghent (BE)

( * ) Notice: Subject to any disclaimer, the term of this patent is extended or adjusted under 35 U.S.C. 154(b) by 1564 days.

(21) Appl. No.: 15/994,305

(22) Filed: May 31, 2018

(65) Prior Publication Data

US 2018/0360367 A1 Dec. 20, 2018

(30) Foreign Application Priority Data

Jun. 14, 2017 (EP) ..................... 17176002

(51) Int. Cl.
*A61B 5/00* (2006.01)
*A61B 5/293* (2021.01)
(Continued)

(52) U.S. Cl.
CPC .......... *A61B 5/4064* (2013.01); *A61B 5/0084* (2013.01); *A61B 5/293* (2021.01);
(Continued)

(58) Field of Classification Search
CPC .... A61N 1/05; A61N 1/0551; A61N 1/36071; A61N 1/0558; A61N 2001/058;
(Continued)

(56) References Cited

U.S. PATENT DOCUMENTS

| | | | |
|---|---|---|---|
| 5,419,777 | A | 5/1995 | Hofling |
| 5,441,481 | A | 8/1995 | Mishra et al. |

(Continued)

FOREIGN PATENT DOCUMENTS

| | | |
|---|---|---|
| WO | 2009/047494 A1 | 4/2009 |
| WO | 2012/154284 A2 | 11/2012 |
| WO | 2014/170338 A1 | 10/2014 |

OTHER PUBLICATIONS

Veen et al. "Macroscopic and microscopic observations of needle insertion into gels". Proceedings of the Institution of Mechanical Engineers. Part H, Journal of engineering in medicine. 226. 441-9 (2012) (Year: 2012).*

(Continued)

*Primary Examiner* — Joseph A Stoklosa
*Assistant Examiner* — Brian M Antiskay
(74) *Attorney, Agent, or Firm* — McDonnell Boehnen Hulbert & Berghoff LLP

(57) ABSTRACT

A brain interaction apparatus is provided. The apparatus comprises a plurality of filaments; and a brain invasive launcher having a plurality of launching channels extending in a longitudinal direction between a proximal end and a distal end thereof. Each launching channel is configured for holding one of the plurality of filaments moveably arranged therein. At least one of the plurality of filaments is provided with a steering tip affixed to a distal end thereof. The steering tip comprises a portion tapering in a longitudinal direction of the at least one of the plurality of filaments thereby narrowing toward a distal end of the steering tip. The tapered portion is rotationally asymmetrical about a longitudinal axis of the at least one of the plurality of filaments.

32 Claims, 6 Drawing Sheets

(51) Int. Cl.
*A61B 17/34* (2006.01)
*A61B 90/10* (2016.01)
*A61M 5/158* (2006.01)
*A61B 10/00* (2006.01)

(52) U.S. Cl.
CPC .......... *A61B 17/3478* (2013.01); *A61B 90/10* (2016.02); *A61M 5/158* (2013.01); *A61B 10/0045* (2013.01); *A61B 2090/103* (2016.02); *A61B 2560/066* (2013.01); *A61M 2005/1585* (2013.01); *A61M 2005/1586* (2013.01); *A61M 2210/0693* (2013.01)

(58) Field of Classification Search
CPC .... A61N 1/048; A61N 1/0488; A61N 1/0529; A61N 1/0534; A61N 1/0539; A61N 1/0526; A61B 17/3468; A61B 2090/3966; A61B 5/4839; A61B 17/3415; A61B 2018/00839; A61B 5/6852; A61B 17/3417; A61B 2017/003; A61B 2018/1425
USPC ......... 600/372–373, 377–378, 381, 544–545
See application file for complete search history.

(56) References Cited

U.S. PATENT DOCUMENTS

| | | | | |
|---|---|---|---|---|
| 6,071,230 | A * | 6/2000 | Henalla | A61F 2/0004 600/29 |
| 8,798,722 | B2 | 8/2014 | Rylander et al. | |
| 9,339,331 | B2 * | 5/2016 | Tegg | A61B 18/1492 |
| 2002/0026127 | A1 * | 2/2002 | Balbierz | A61B 18/1477 600/567 |
| 2004/0064098 | A1 | 4/2004 | Cuschieri et al. | |
| 2005/0251144 | A1 * | 11/2005 | Wilson | A61B 17/3403 606/108 |
| 2006/0015067 | A1 | 1/2006 | Bates | |
| 2007/0106143 | A1 * | 5/2007 | Flaherty | A61N 1/0531 607/116 |
| 2007/0232988 | A1 * | 10/2007 | Zapata | A61B 17/34 604/26 |
| 2009/0012477 | A1 * | 1/2009 | Norton | A61B 17/3423 604/174 |
| 2009/0326519 | A1 * | 12/2009 | Wilson | A61M 39/0247 606/1 |
| 2010/0191305 | A1 * | 7/2010 | Imran | A61B 5/291 607/45 |
| 2010/0222668 | A1 | 9/2010 | Dalke et al. | |
| 2010/0280494 | A1 | 11/2010 | Matsuura et al. | |
| 2011/0224607 | A1 | 9/2011 | Vogelbaum et al. | |
| 2012/0245529 | A1 | 9/2012 | Hummen et al. | |
| 2012/0316628 | A1 | 12/2012 | Lopez | |
| 2015/0119674 | A1 * | 4/2015 | Fischell | A61B 5/6852 606/41 |
| 2016/0346513 | A1 | 12/2016 | Swaney et al. | |

OTHER PUBLICATIONS

Partial European Search Report, received from the European Patent Office, dated Dec. 22, 2017, for European Application No. 17176002.8, pp. 1-11.
Extended European Search Report, received from the European Patent Office, dated Feb. 27, 2018, for European Application No. 17176002.8, pp. 1-13.

* cited by examiner

BRAIN INTERACTION APPARATUS, CRANIAL ANCHOR, AND RELATED SYSTEMS AND METHODS

CROSS-REFERENCE

This application claims priority from EP patent application no. 17176002.8, filed Jun. 14, 2017, which is incorporated by reference in its entirety.

TECHNICAL FIELD

The present disclosure described herein generally relates to the field of brain interaction apparatuses and, more particularly, to a brain interaction apparatus comprising a plurality of filaments, to cranial anchors, and to related systems and methods.

BACKGROUND

Catheters have been used for many years to deliver therapeutic agents to patients. In many instances, catheters are implanted in patients that have been diagnosed with diseases that require long-term therapeutic treatment, for example brain tumors. When treating these types of diseases, a need arises to deliver therapeutic drugs to multiple locations simultaneously. Current technology requires the use of multiple separate catheters and pumps to ensure the equal delivery of therapeutics to the tumor and the outlying tissues.

Additionally, in some cases it is necessary to obtain several samples over a period of time in order to determine the type of disease and monitor its progress. Such surgical procedures carry an intrinsically high level of risk of infection and hemorrhage.

An example of a catheter assembly aimed at reducing the risk of hemorrhage or tissue trauma is disclosed in US application US2011/0224607A. The catheter assembly comprises a first catheter including a wall with an inner surface, and a second catheter connected to the wall of the first catheter and disposed outward of the inner surface of the wall.

PCT application WO2014170338 discloses another type of a surgical instrument used for invasive maneuvers in the body of a patient. The multi-cannula surgical instrument disclosed in this document functions either as an electrocautery instrument or as a safety needle. The multi-cannula surgical instrument comprises a rigid outer cannula, and an inner cannula. The inner cannula further comprises one or more first inner ducts and one or more first flow-through orifices near a distal tip of the inner cannula.

Further, in US 2010/0222668A1 a catheter system adapted for navigating, guiding, and implanting a catheter or a plurality of catheters in a spatially defined implantation within the tissue of a patient is provided. The system can include a tissue navigation system and a probe to inform the navigation system to guide emplacement of the catheters within a target tissue. The probe can provide images, such as fiber-optic visual images, or ultrasound images, or can provide radiolocation data, to guide the catheter emplacement. The catheters supply a pressurized liquid including a bioactive agent, such as can be used in the treatment of cancer, for example 1231- or 1251-IUDR. The system and methods provided can be used in the treatment of locally advanced tumors, such as cancers of the brain, head or neck, esophagus, prostate, ovary, liver, pancreas, bladder or rectum.

However, there exists a significant need for improved techniques related to brain interaction apparatuses in order to minimize the invasiveness of procedures in the brain of a patient. Further, there is a need for increased accuracy of such procedures in order to gain a better understanding of diseases and ultimately select an appropriate treatment. Still further, there is a need to improve brain interaction apparatuses with respect to size and ease of application to the skull and brain of a patient.

SUMMARY OF THE DISCLOSURE

It is an object of the present disclosure to mitigate, alleviate or eliminate one or more of the above-identified deficiencies in the art and disadvantages singly or in combination. According to a first aspect of the disclosure, these and other objects are achieved in full, or at least in part, by a brain interaction apparatus, comprising a plurality of filaments; a brain invasive launcher having a plurality of launching channels extending in a longitudinal direction between a proximal end and a distal end thereof, each launching channel being configured for holding a filament moveably arranged therein, the filament being one of the plurality of filaments; wherein at least one of the plurality of filaments is provided with a steering tip affixed to a distal end thereof, wherein the steering tip comprises a portion tapering in a longitudinal direction of the at least one of the plurality of filaments thereby narrowing toward a distal end of the steering tip, the tapered portion being rotationally asymmetrical about a longitudinal axis of the at least one of the plurality of filaments.

The distal end of the steering tip may be offset from the longitudinal axis of the at least one of the plurality of filaments.

Further, the brain invasive launcher may comprise a launcher position indicator configured to determine a location of the brain invasive launcher in a brain of a subject.

The at least one of the plurality of filaments may be configured to be in an installation state, in which the filament is housed in the launching channel, and a working state, in which the filament is extended beyond the distal end of the brain invasive launcher when the same is in a fixed position.

The at least one of the plurality of filaments may comprise a plurality of apertures.

The steering tip may comprise a steering tip position indicator configured to determine a location of the steering tip and/or the at least one of the plurality of filaments in a brain of a subject.

The at least one of the plurality of filaments may be configured to collect measurement data.

The at least one of the plurality of filaments may be an optical fiber.

The at least one of the plurality of filaments may be an electrical wire.

The brain interaction apparatus may further comprise a multi-lumen stylet connected to the brain invasive launcher, wherein the multi-lumen stylet comprises a plurality of channels configured for holding the plurality of filaments, and wherein the plurality of channels is aligned with the plurality of launching channels of the brain invasive launcher.

According to a second aspect it is provided a cranial anchor for a brain interaction apparatus according to the first aspect, the cranial anchor being configured to be secured to a skull of a subject, the cranial anchor comprising a proximal end forming an outer flange; an elongated distal end for inserting into a skull aperture, wherein an axial lumen is provided, the axial lumen being tapered in a longitudinal direction of the cranial anchor and narrowing toward the distal end; wherein the proximal end comprises at least one groove extending from the circumference of the outer flange toward a central axis of the cranial anchor, and wherein the axial lumen is configured for receiving and guiding the brain invasive launcher, and wherein the axial lumen provides a pivot point for directing the brain invasive launcher.

The elongated distal end may be provided with a narrowed section having a diameter adjusted to a diameter of the multi-stylet such that the plurality of filaments is brought into the channels.

The narrowed section may provide a pivotal point for the multi-stylet.

According to a third aspect it is provided a system comprising; a brain interaction apparatus according to the first aspect; a cranial anchor according to the second aspect; a data receiving unit configured to receive measurement data collected by the at least one of the plurality of filaments; a data storing unit configured to store the measurement data received by the data receiving unit; a data analyzing unit configured to analyze the measurement data in order to determine a setup of collection of biological material, and/or a setup of collection of data, and/or a setup of injection of at least one substance.

According to a fourth aspect it is provided a method comprising providing a cranial anchor according to the second aspect inserted in a skull of a subject; providing a brain interaction apparatus according to the first aspect; connecting the brain invasive launcher to the cranial anchor, thereby having at least the brain invasive launcher entering the brain of the subject; feeding at least one of the plurality of filaments beyond the distal end of the brain invasive launcher in a trajectory in relation to the brain invasive launcher while the same remains in a fixed position, thereby reaching a pre-determined location of the brain.

The step of extending at least one of the plurality of filaments may comprise rotating the at least one of the plurality of filaments along its longitudinal axis in order to adjust the trajectory and arrive at the pre-determined location.

The method may further comprise collecting data and/or biological material associated with the pre-determined location via the at least one of the plurality of filaments, and analyzing the collected data and/or biological material in order to determine a setup of the collection of biological material, and/or a setup of the collection of data, and/or a setup of the injection of the least one substance.

The step of collecting data and/or biological material may be performed during a collection phase being at least 24 hours.

The method may further comprise injecting at least one substance into the brain at one or more injecting locations via the at least one of the plurality of filaments.

The step of injecting at least one substance may be performed during an injection phase being at least 24 hours.

The method may further comprise filling an upper portion of the axial lumen with an inert, resilient material in order to seal the brain interaction apparatus from an external environment.

According to a fifth aspect it is provided a kit of parts comprising: a brain interaction apparatus according to the first aspect; wherein the kit of parts comprises at least two types of filaments, and wherein the kit of parts comprises at least two types of steering tips.

The kit of parts may further comprise at least two types of cranial anchors according to the second aspect.

According to a sixth aspect it is provided a method for providing decision support in diagnosing or treating a brain disease, the method comprising collecting measurement data from at least one location in a brain, transferring location data and the measurement data to a data processing device connected to a data storage device, wherein the data storage device comprises a time series of location data and measurement data collected from other brains, comparing the location data and the measurement data with the time series of location data and measurement data collected from other brains, based on the comparison, providing location data for a subsequent measurement, or providing a diagnosis, or providing location data for injection of at least one substance.

The step of collecting measurement data may be performed during a period of at least 24 hours.

A feature described in relation to one aspect may also be incorporated in other aspects, and the advantage of the feature is applicable to all aspects in which it is incorporated.

Other objectives, features and advantages of the present disclosure will appear from the following detailed disclosure, from the attached claims as well as from the drawings.

Generally, all terms used in the claims are to be interpreted according to their ordinary meaning in the technical field, unless explicitly defined otherwise herein. Further, the use of terms "first", "second", and "third", and the like, herein do not denote any order, quantity, or importance, but rather are used to distinguish one element from another. All references to "a/an/the [element, device, component, means, step, etc.]" are to be interpreted openly as referring to at least one instance of said element, device, component, means, step, etc., unless explicitly stated otherwise. The steps of any method disclosed herein do not have to be performed in the exact order disclosed, unless explicitly stated.

BRIEF DESCRIPTION OF THE DRAWINGS

The above, as well as additional objects, features and advantages of the present disclosure, will be better understood through the following illustrative and non-limiting detailed description of different embodiments of the present disclosure, with reference to the appended drawings, wherein.

DETAILED DESCRIPTION

Figures 1A, 1B:
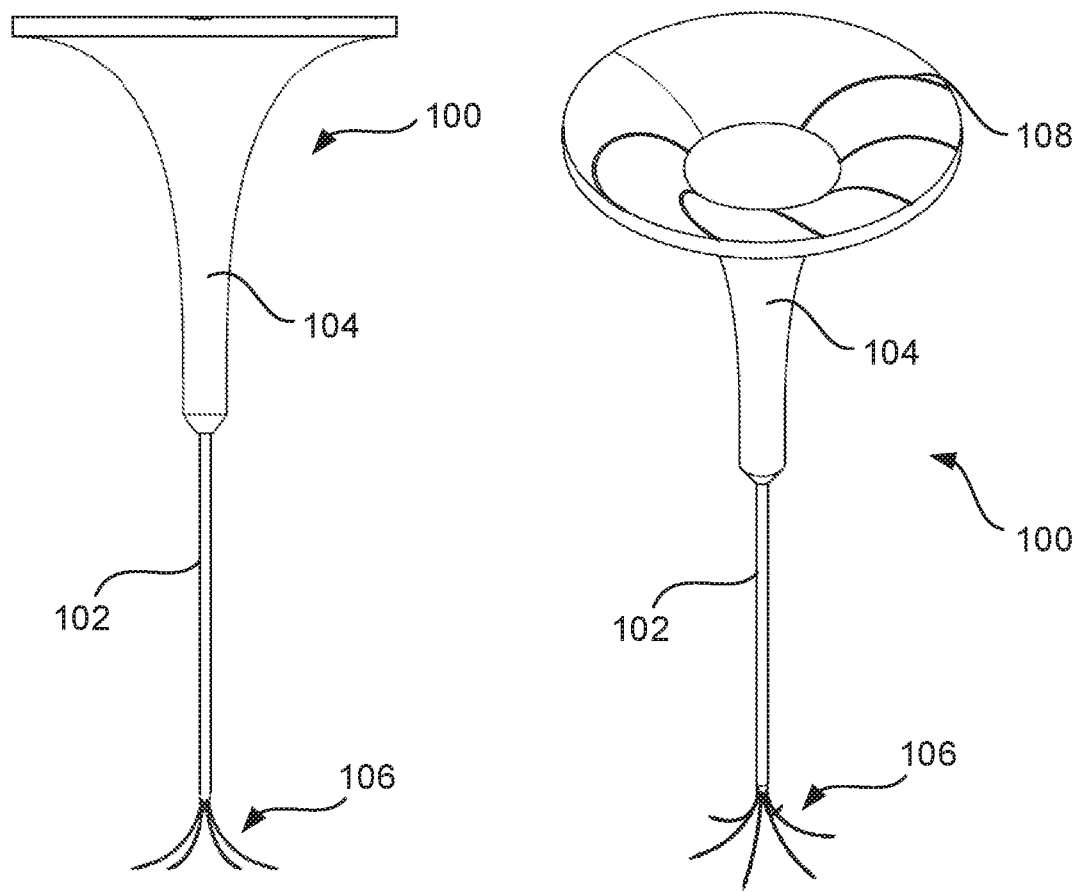
FIG. 1a schematically illustrates a side view of an example embodiment of a brain interaction apparatus and a cranial anchor.
FIG. 1b schematically illustrates a perspective view of an example embodiment of a brain interaction apparatus and a cranial anchor.
Figures 1C, 1D:
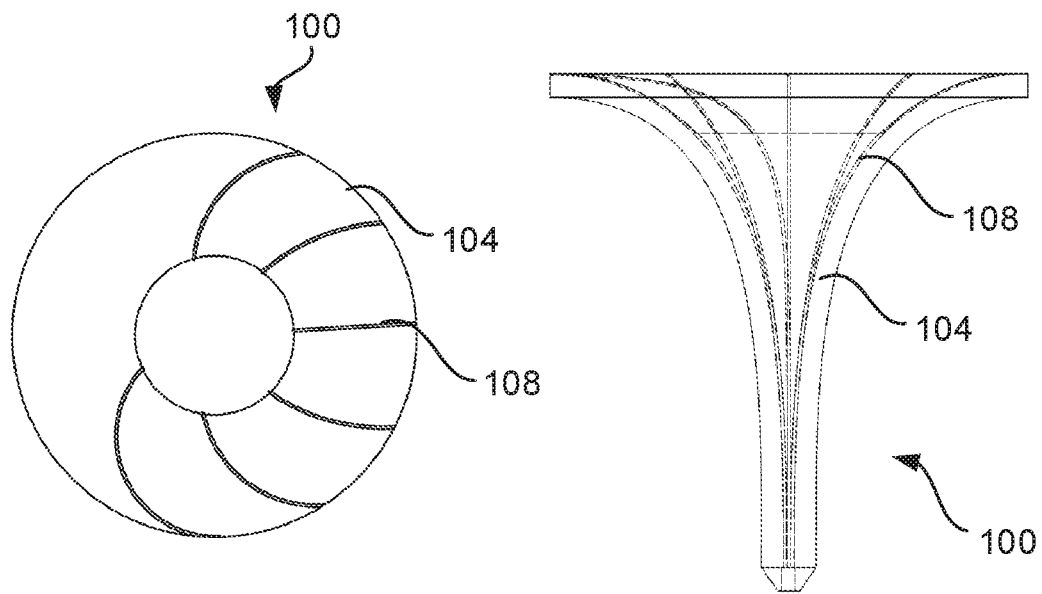
FIG. 1c schematically illustrates a top view of an example embodiment of a cranial anchor.
FIG. 1d schematically illustrates a side view of an example embodiment of a cranial anchor.

FIGS. 1a and 1b generally illustrate an example embodiment of system 100 comprising a brain invasive launcher 102 and a cranial anchor 104 for providing filaments 106 into a brain such that measurement data or biological samples can be collected or such that a medical substance can be injected with a high degree of location accuracy. In FIGS. 1c and 1d, the cranial anchor 104 is illustrated in isolation.

The system 100 may be applied by providing an aperture in a skull and thereafter inserting the cranial anchor 104 into the hole. In order to be securely attached to the skull, the cranial anchor 104 may be provided with a flange that rests against the skull when the cranial anchor is inserted. Further, the cranial anchor may be rotationally symmetric and have side walls sloping inwards, as illustrated. One potential benefit of these features is that the filaments 106 can be gradually redirected approximately 90 degrees from being fed in parallel with a skull surface outside the skull to being fed in parallel with a normal of the skull surface inside the skull. This in turn implies that the filaments may lay close to the skull when measurement data or samples are collected or when substance is injected, which both reduces a risk that the filaments are unintentionally displaced and increases the comfort of a patient.

In order to guide the filaments, grooves 108 may be provided in the cranial anchor. These grooves 108 may in a distal end of the cranial anchor be aligned with launching channels of the brain invasive launcher 102 such that the filaments may smoothly be transferred from the cranial anchor to the brain interaction apparatus.

In order to make sure that the pre-determined location can be reached with a high degree of accuracy, a launcher position indicator may be used. The launcher position indicator may be achieved in different ways. It may be achieved mechanically by having a recess provided in the brain invasive launcher 102 and a protrusion in the cranial anchor 104, or vice versa, such that a sound is formed which in turn an operator is notified acoustically and/or tactilely that the brain invasive launcher is correctly provided in the cranial anchor 104. After having made sure that the brain invasive launcher 102 is correctly mounted with respect to the cranial anchor 104, a location of a distal end of the brain invasive launcher 102 can be determined with high degree of accuracy.

Figure 2:
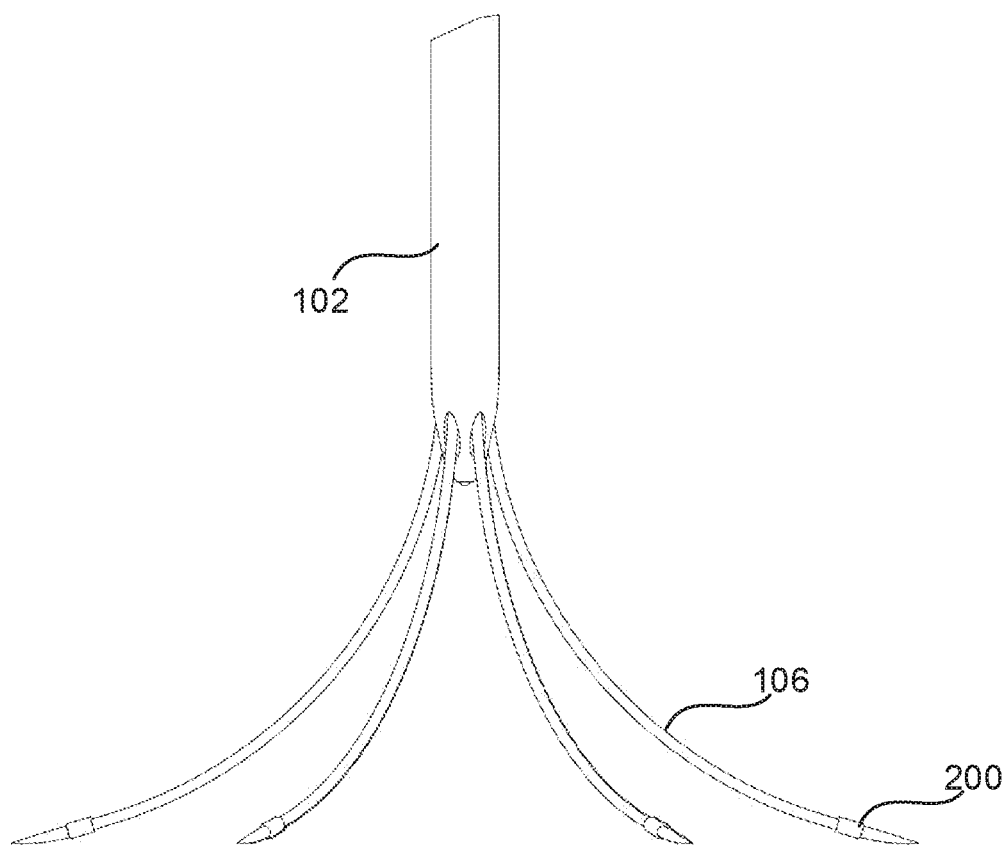
FIG. 2 schematically illustrates an example embodiment of a brain interaction apparatus.

As illustrated in FIG. 2, in order to be able to steer the filaments 106 to final positions within the brain, in one embodiment, each of the filaments may be provided with steering tips 200. The steering tips 200 are designed to be rotationally asymmetrical, which has the effect that they move into the brain along a preset trajectory. In order to be able to precisely guide the filaments into the brain, the steering tips may be exchangeable, which means e.g. that if a sharp trajectory is preferred, i.e. a path having a high degree of curvature, a steering tip with a palpable rotational asymmetry may be chosen.

Figure 3A:
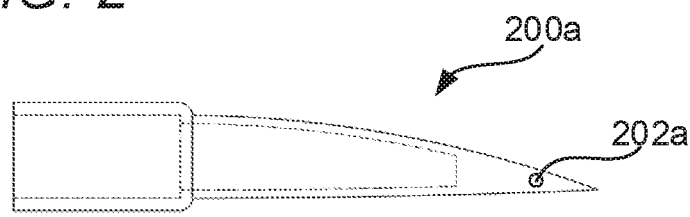
FIG. 3a schematically illustrates a side view of an example embodiment of a steering tip.
Figure 3B:
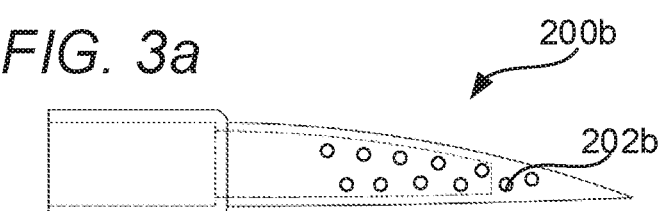
FIG. 3b schematically illustrates a side view of an example embodiment of a steering tip.

As illustrated in FIGS. 3a to 3d, the steering tips 200 may come in different designs and shapes. As illustrated in FIG. 3a, a steering tip 200a, according to a first embodiment, may have a distal end being offset with respect to a longitudinal center axis and may be provided with one aperture, such as a micro pore, for injecting substances into the brain or for receiving a biological sample e.g. in the form of a suspension or other fluid or semi-fluid containing biological material. In FIG. 3b, a steering tip 200b according to a second embodiment is illustrated. Unlike the steering tip 200a according to the first embodiment, the steering tip 200b may be provided with a plurality of apertures 202b, such as micro-pores, such that biological material can be gathered quicker or such that substances can be injected over a larger area at the same time. In addition, an advantage of having the plurality of apertures is that a flow may be distributed over a larger area, which makes higher flow rates possible. Further, another positive effect of having the flow distributed over a larger area is that a risk of tissue damage can be reduced.

Figure 3C:
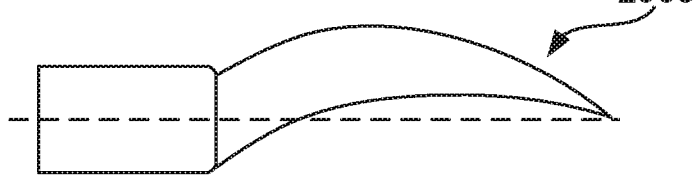
FIG. 3c schematically illustrates a side view of an example embodiment of a steering tip.
Figure 3D:
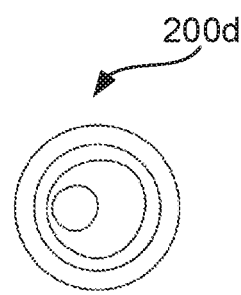
FIG. 3d schematically illustrates a top view of an example embodiment of a steering tip.

In FIG. 3c, a steering tip 200c is illustrated. Unlike the steering tips 200a, 200b according to the first and second embodiments, the steering tip 200c according to a third embodiment is not provided with a distal end offset with respect to a longitudinal center axis, but instead being curved such that when being fed into the brain curvature will give rise to that the filament to which the steering tip is attached moves along a trajectory. Thus, providing for that the filament is following the trajectory does not require the steering tip to be placed off-set with respect to the longitudinal center axis. In FIG. 3d, a top view of a steering tip 200d according to a fourth embodiment is illustrated. Similar to the steering tips 200a, 200b according to the first and second examples, a distal end is offset with respect to a longitudinal center axis.

As mentioned above, the apertures may be micro-pores. Micro-pores used for delivering substances may range from 0.5 μm to 2 μm, and micro-pores used for collecting biological samples may range from 2 μm to 30 μm. Further, in order to provide for that the micro-pores for collecting are at reduced risk of being clogged these may have an anti-clogging design.

Having micro-pores that are fabricated provides an advantage compared to e.g. porous polysulfane in that shape and size can be precisely controlled, which in turn provides for that injecting substances can be made with a high degree of accuracy.

Figure 4A:
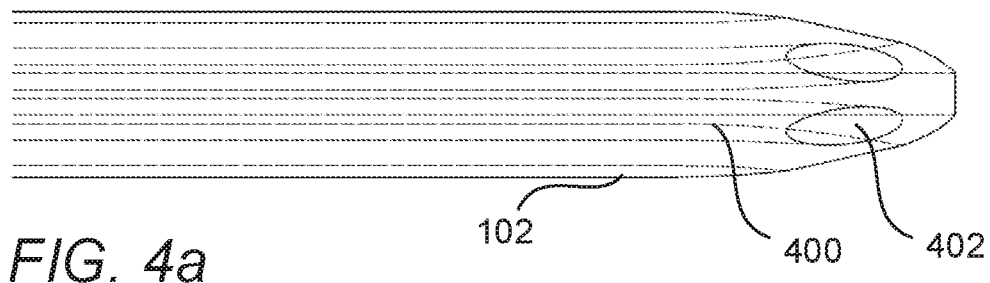
FIG. 4a schematically illustrates a side view of an example embodiment of a brain invasive launcher.
Figure 4B:
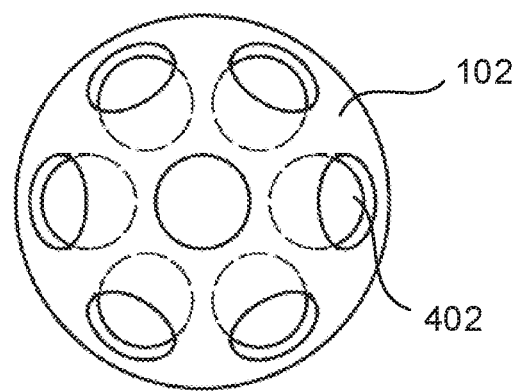
FIG. 4b schematically illustrates a side view of an example embodiment of a brain invasive launcher.

In order to provide for that the filaments can reach locations of the brain with high accuracy launching channels 400 of the brain invasive launcher 102 can have exit holes 402 at well-defined angles and directed in chosen directions, as illustrated for instance in FIGS. 4a and 4b.

Figure 5:
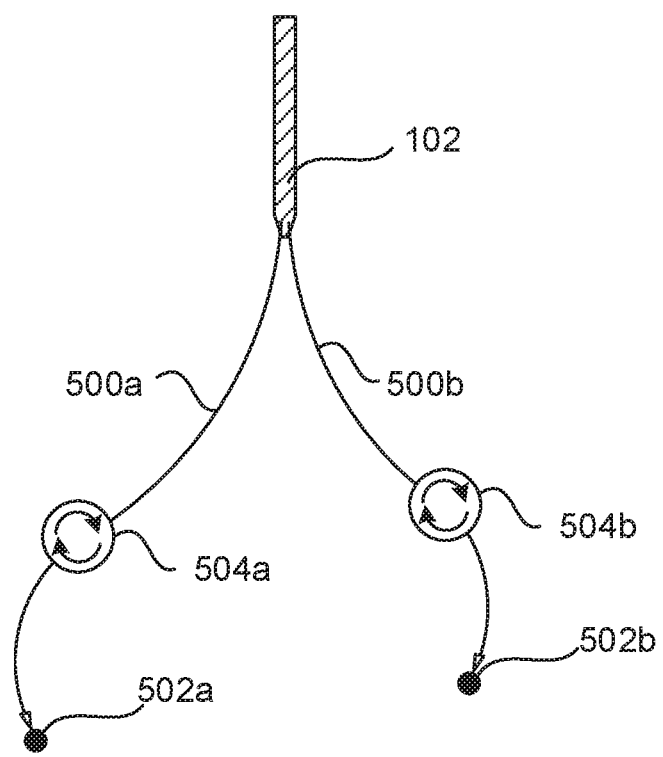
FIG. 5 schematically illustrates a two-dimensional representation of an example embodiment of a plurality of filaments and respective trajectories.

FIG. 5 schematically illustrates an example embodiment of how trajectories along which the filaments are inserted can be controlled. After having placed the brain invasive launcher 102 in the cranial anchor (not shown in FIG. 5) the filaments can be fed into the brain, and due to the rotational asymmetry of the steering tips the filaments can move along well defined trajectories.

In order to change a path 500a of a first filament to reach a first location 502a, the first filament may be rotated a pre-set number of degrees in a first rotation location 504a such that the path 500a is changed. In the same manner, a path 500b of a second filament to reach a second location 502b may be changed by being rotated in a second rotation location 504b.

Figures 6A, 6B:
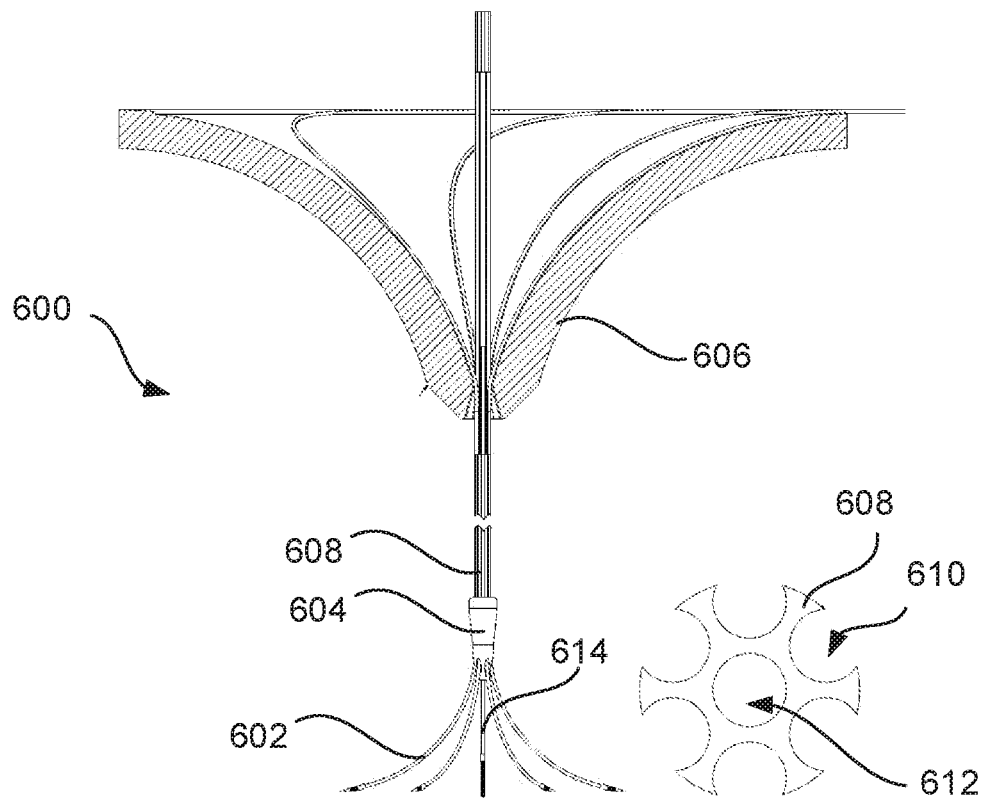
FIG. 6a schematically illustrates a cross-sectional view of another example embodiment of a combination of a brain interaction apparatus and a cranial anchor.
FIG. 6b illustrates a cross-section of an example embodiment of multi-lumen stylet.

FIG. 6a illustrates an example embodiments of a system 600 for providing filaments 602 into the brain, wherein the system comprises a brain invasive launcher 604 connected to a cranial anchor 606 similar to the system 100 illustrated in FIG. 1a and FIG. 1b. However, unlike the system 100, the brain invasive launcher 604 can be combined with a multi-lumen stylet 608, further illustrated in FIG. 6b, such that the filaments can be fed into grooves 610, or other types of channels, of the multi-lumen stylet as the brain invasive launcher 604 and the multi-lumen stylet 608 are fed into the brain.

Further, a central channel 612 of the multi-lumen stylet 608 may be provided for a central filament 614. The central filament may be of a different type than the other filaments 602. For instance, the central filament 614 may be a filament configured for gathering biological material and the other filaments 602 may be electrodes for collecting electric impulse data. Even though only illustrated together with the multi-lumen stylet 608, the central channel 612 may also be used in systems without the multi-lumen stylet 608, such as the system 100 illustrated in FIG. 1a and FIG. 1b. Further, the central filament 614 and the central channel 612 does not necessarily have to be placed centrally, but may in other embodiments than the example embodiment illustrated in FIG. 6a be placed in a non-central location. In addition, even though one central channel 612 and central filament 614 are illustrated, several channels and filaments like the central channel 612 and the central filament 614 may be used as well.

Figures 7A, 7B, 7C:
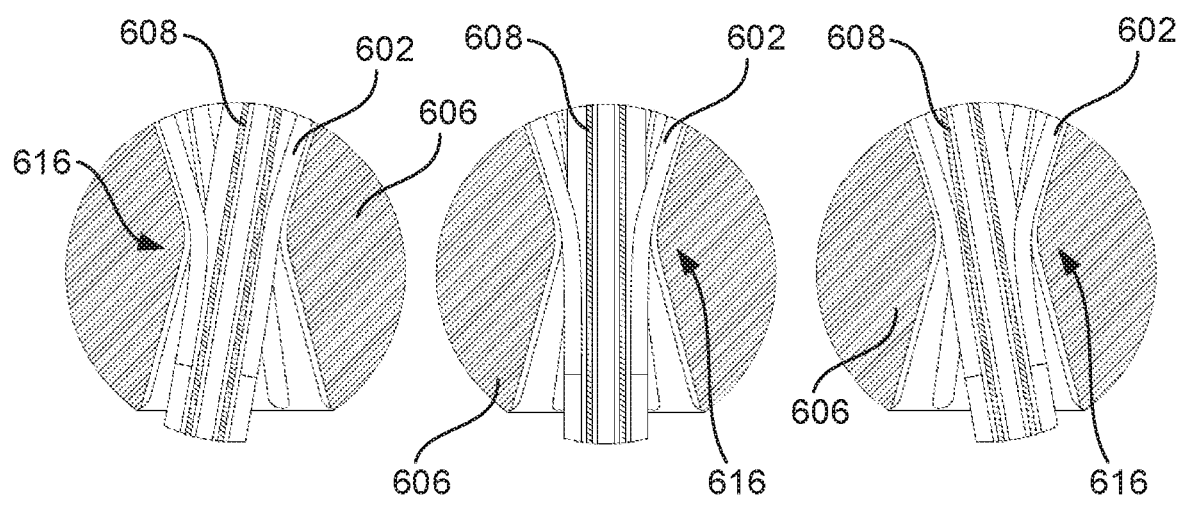
FIGS. 7a, 7b and 7c illustrates an example embodiment of narrowed section of the cranial anchor of FIG. 6 in further detail.

In order to provide for that the filaments 602 are properly fed into the grooves 610 of the multi-lumen stylet 608, in one embodiment, a narrowed section 616 may be provided in the cranial anchor 606, as illustrated in FIGS. 7a-7c. In addition to pushing the filaments 602 into the grooves 610, the narrowed section 616 may also serve as a pivotal point for the multi-lumen stylet as illustrated in FIGS. 7a-7c. By having the possibility to pivot the multi-lumen stylet around the narrowed section 616, a number of different path options can be increased. Even though only illustrated for the system 600 comprising the multi-lumen stylet 608, the concept of having the narrowed section 616 such that pivoting is made possible is also applicable to, for instance, the example embodiment system 100 illustrated in FIGS. 1a and 1b.

The multi-lumen stylet 608 may, after the filaments 602 have been introduced, be removed by carefully withdrawing the multi-lumen stylet 608 out from the brain via the cranial anchor 606 or, alternatively, the multi-lumen stylet 608 may be left in situ. An alternative option would be to partly remove the multi-lumen stylet; that is, withdrawing part of the multi-lumen stylet and leaving part of multi-lumen stylet in situ.

Having the multi-lumen stylet 608 provided with individual grooves, or other channels, for the filaments 602 reduces a risk that the filaments may become stuck when introducing or removing these compared to when the same channel is used for multiple filaments.

In order to be able to individually adapt the system 600, as well as the system 100, the different parts of the systems may come in different sizes and shapes. For instance, a child skull may require a small cranial anchor; in order to reach deep into the brain, an elongated brain invasive launcher may be needed; in order to collect measurement data in the form of electric pulses, filaments in the form of electrodes may be needed; in order to be able to follow a set path in the brain, a steering tip with a rotational asymmetry making it possible to closely follow this set path may be chosen, etc. Thus, having a modular system, like the example embodiment systems 100, and 600 illustrated in FIGS. 1a-1b and FIG. 6a, makes it possible to provide a high degree of individual adjustment.

Both the example embodiments systems 100, and 600 illustrated in FIG. 1 and FIG. 6, respectively, may form part of a system for determining a setup for collection of biological material, and/or a setup for collection of measurement data, and/or a setup of injection of at least one substance in a subsequent step. In addition to the brain interaction apparatus and the cranial anchor, the system may comprise a data receiving unit configured to receive the measurement data collected by the at least one of the plurality of filaments, and a data storing unit configured to store the measurement data received by the data receiving unit, and a data analyzing unit configured to analyze the measurement data in order to determine the setup for collection of biological material, and/or a setup for collection of measurement data, and/or a setup for injection of at least one substance. The set-up may in this context be related to any information directly or indirectly related to when, where and how collection of biological material can be made in a subsequent step in order to achieve a better understanding of a condition of the brain, or directly or indirectly related to when, where and how collection of measurement data can be made in a subsequent step in order to achieve a better understanding of a condition of the brain, or directly or indirectly related to when, where and how injection of at least one substance can be made in a subsequent step in order improve the condition of the brain.

Figure 8:
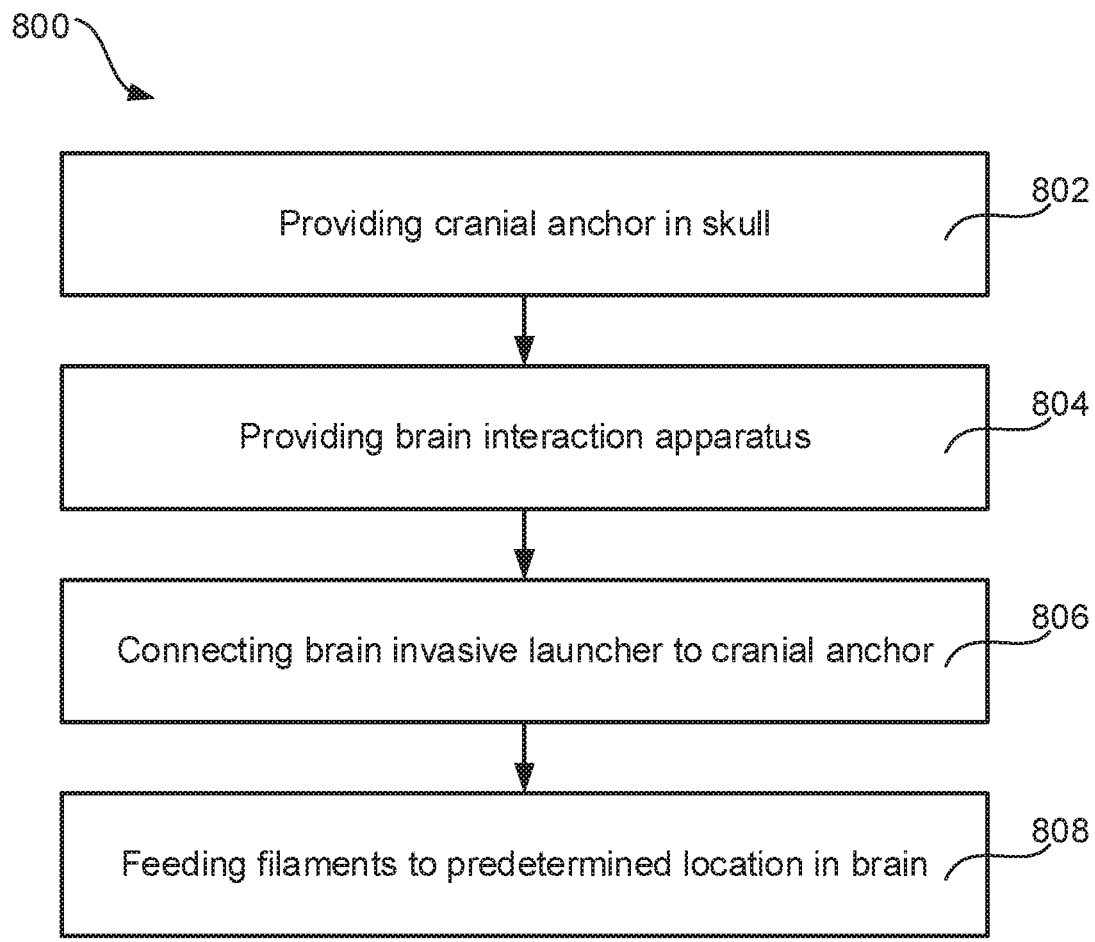
FIG. 8 is a flow chart illustrating an example embodiment of method for reaching a pre-determined location of a brain by using a brain interaction apparatus and a cranial anchor.

FIG. 8 generally illustrates an example embodiment general method 800 for reaching a pre-determined location of the brain in order to be able to collect measurement data in order to e.g., make a diagnosis, or to collect a biological sample or to inject substances, may comprise providing a cranial anchor in the skull 802, providing a brain interaction apparatus comprising a brain invasive launcher and filaments 804, connecting the brain invasive launcher to the cranial anchor 806, and feeding the at least one of the filaments from the brain invasive launcher into the brain to the pre-determined location 808.

Having the possibility to reach a location of the brain with high accuracy makes it possible to collect reliable data from different parts of the brain during a period of time. This data can be compared with other data collected from other brains in order to suggest a likely diagnosis or a treatment plan likely to work, but also in the case a tumor is present in the brain, a likely placement of the tumor and a likely evolvement of the tumor.

Figure 9:
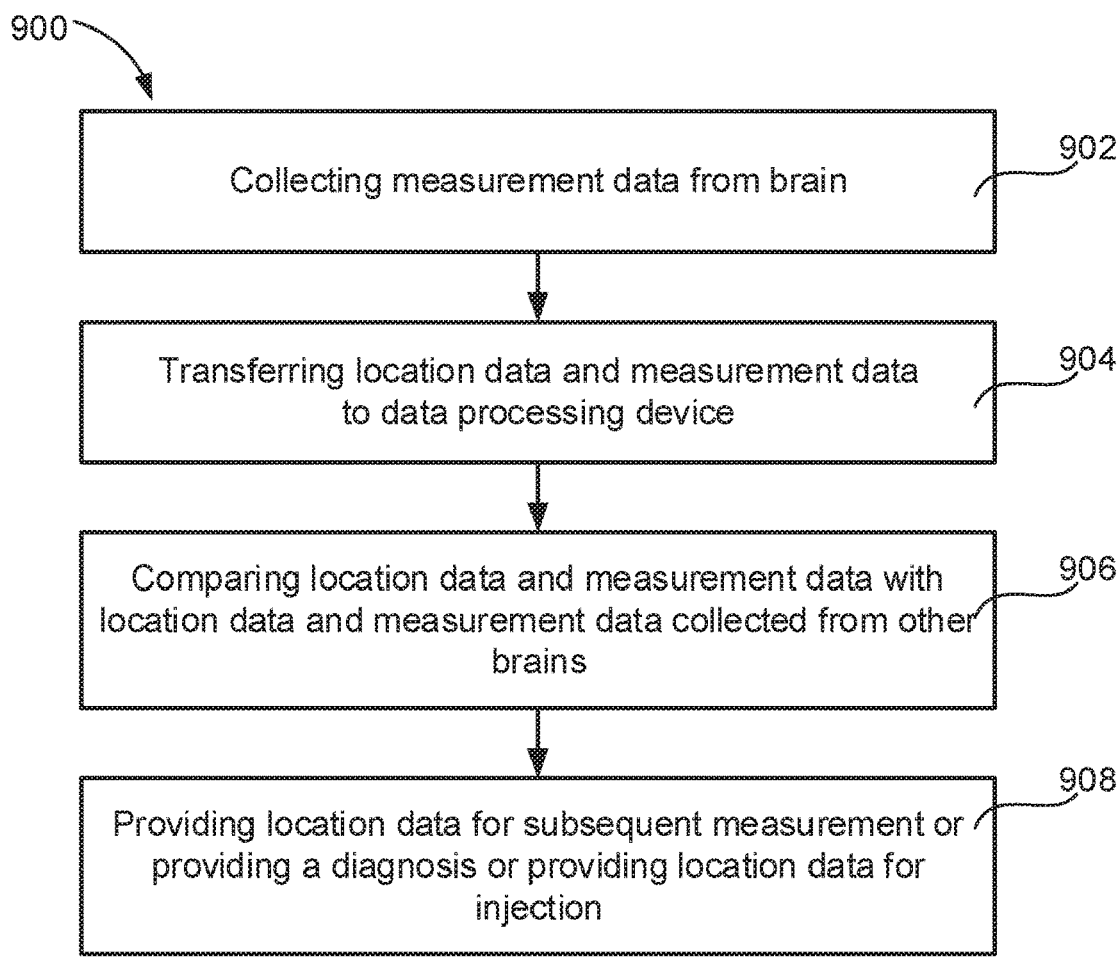
FIG. 9 is a flowchart illustrating an example embodiment of method for assisted decision support.

FIG. 9 generally illustrates an example embodiment of a method for providing decision support. The method 900 may comprise collecting measurement data from the brain 902, e.g. by using any of the systems or methods described herein, transferring location data and measurement data to a data processing device 904, comparing the location data and the measurement data with location data and measurement data collected from other brains 906, and providing a location data for subsequent measurement or providing a diagnosis or providing location data for injection 908.

Figure 10:
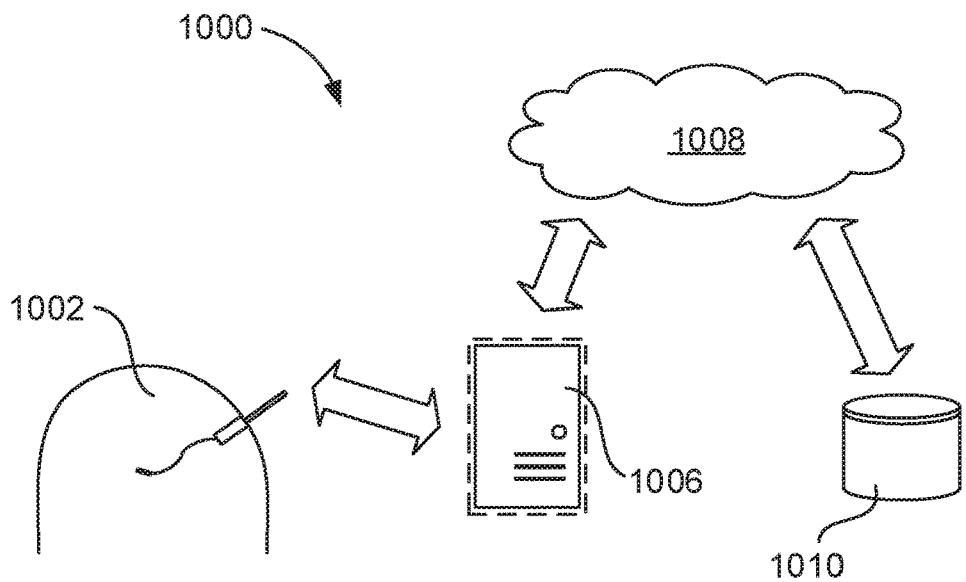
FIG. 10 generally illustrates an example embodiment of system for implanting the method according to the flowchart of FIG. 9.

In order to implement the method 900 illustrated in FIG. 9, an example embodiment of system 1000 generally illustrated in FIG. 10 may be used. In order to collect the location data and the measurement data, a system 1002 attached to the skull of a patient may be used. The system 1002 may comprise the systems 100, 600 illustrated in FIGS. 1*a*-1*b* and FIG. 6*a* in order to collect the location and measurement data.

After having collected the data, the collected data can be sent to a data processing device 1006, e.g. a server. In order to analyze the data collected from the brain, location data and measurement data collected from other brains can be downloaded and compared to the data collected from the brain. The data collected from other brains may be downloaded via a data communications network 1008 and the data collected from other brains may be stored on a data storage device 1010.

The present disclosure has mainly been described above with reference to a few embodiments. However, as is readily appreciated by a person skilled in the art, other embodiments than the ones disclosed above are equally possible within the scope of the present disclosure, as defined by the appended patent claims.

The invention claimed is:

1. A system comprising;
a brain interaction apparatus comprising:
a plurality of filaments;
a brain invasive launcher having a plurality of launching channels extending in a longitudinal direction between a proximal end and a distal end thereof, each launching channel being configured for holding one of the plurality of filaments moveably arranged therein; and
a steering tip affixed to a distal end thereof of at least one of the plurality of filaments, wherein the steering tip comprises a portion tapering in a longitudinal direction of the at least one of the plurality of filaments thereby narrowing toward a distal end of the steering tip, the tapered portion being rotationally asymmetrical about a longitudinal axis of the at least one of the plurality of filaments and configured for guiding the at least one of the plurality of filaments along a pre-set trajectory; and
a cranial anchor for the brain interaction apparatus, the cranial anchor being configured to be secured to a skull of a subject, the cranial anchor comprising
a proximal end forming an outer flange;
an elongated distal end for inserting into a skull aperture, wherein an axial lumen is provided, the axial lumen being tapered in a longitudinal direction of the cranial anchor and narrowing toward the distal end;
wherein the proximal end comprises at least one groove extending from the circumference of the outer flange toward a central axis of the cranial anchor, the at least one groove is configured for aligning, at the distal end of the cranial anchor, with at least one of the plurality of launching channels of the brain invasive launcher and for receiving and guiding the at least one of the plurality of filaments into the least one of the plurality of launching channels, and wherein the axial lumen is configured for receiving and guiding the brain invasive launcher, and wherein the axial lumen provides a pivot point for directing the brain invasive launcher.

2. The system according to claim 1, wherein the distal end of the steering tip is offset from the longitudinal axis of the at least one of the plurality of filaments.

3. The system according to claim 1, wherein the brain invasive launcher comprises a launcher position indicator configured to determine a location of the brain invasive launcher in a brain of a subject.

4. The system according to claim 1, wherein the at least one of the plurality of filaments is configured to be in an installation state, in which the filament is housed in the launching channel, and a working state, in which the filament is extended beyond the distal end of the brain invasive launcher when the same is in a fixed position.

5. The system according to claim 1, wherein the at least one of the plurality of filaments comprises a plurality of apertures.

6. The system according to claim 1, wherein the steering tip comprises a steering tip position indicator configured to determine a location of the steering tip, a location of the at least one of the plurality of filaments, or both in a brain of a subject.

7. The system according to claim 1, wherein the at least one of the plurality of filaments is configured to collect measurement data.

8. The system according to claim 7, wherein the at least one of the plurality of filaments is an optical fiber.

9. The system according to claim 7, wherein the at least one of the plurality of filaments is an electrical wire.

10. The system according to claim 1, further comprising a multi-lumen stylet connected to the brain invasive launcher, wherein the multi-lumen stylet comprises a plurality of channels configured for holding the plurality of filaments, and wherein the plurality of channels is aligned with the plurality of launching channels of the brain invasive launcher.

11. The system according to claim 1, wherein the brain interaction apparatus further comprises a multi-lumen stylet connected to the brain invasive launcher, wherein the multi-lumen stylet comprises a plurality of channels configured for holding the plurality of filaments, and wherein the plurality of channels is aligned with the plurality of launching channels of the brain invasive launcher, and wherein the elongated distal end is provided with a narrowed section having a diameter adjusted to a diameter of the multi-lumen stylet such that the plurality of filaments is brought into the channels.

12. The system according to claim 11, wherein the narrowed section provides a pivotal point for the multi-lumen stylet.

13. A system comprising;
a brain interaction apparatus comprising:
a plurality of filaments;
a brain invasive launcher having a plurality of launching channels extending in a longitudinal direction between a proximal end and a distal end thereof, each launching channel being configured for holding one of the plurality of filaments moveably arranged therein; and
a steering tip affixed to a distal end thereof of at least one of the plurality of filaments, wherein the steering tip comprises a portion tapering in a longitudinal direction of the at least one of the plurality of filaments thereby narrowing toward a distal end of the steering tip, the tapered portion being rotationally asymmetrical about a longitudinal axis of the at least one of the plurality of filaments and configured for guiding the at least one of the plurality of filaments along a pre-set trajectory;

a cranial anchor for the brain interaction apparatus, the cranial anchor being configured to be secured to a skull of a subject, the cranial anchor comprising
a proximal end forming an outer flange;
an elongated distal end for inserting into a skull aperture, wherein an axial lumen is provided, the axial lumen being tapered in a longitudinal direction of the cranial anchor and narrowing toward the distal end;
wherein the proximal end comprises at least one groove extending from the circumference of the outer flange toward a central axis of the cranial anchor, the at least one groove is configured for aligning, at the distal end of the cranial anchor, with at least one of the plurality of launching channels of the brain invasive launcher and for receiving and guiding the at least one of the plurality of filaments into the least one of the plurality of launching channels, and wherein the axial lumen is configured for receiving and guiding the brain invasive launcher, and wherein the axial lumen provides a pivot point for directing the brain invasive launcher;
a data receiving unit configured to receive measurement data collected by the at least one of the plurality of filaments;
a data storing unit configured to store the measurement data received by the data receiving unit; and
a data analyzing unit configured to analyze the measurement data in order to determine a setup of collection of biological material, and/or a setup of collection of data, and/or a setup of injection of at least one substance.

14. A kit of parts comprising:
a brain interaction apparatus comprising:
a plurality of filaments;
a brain invasive launcher having a plurality of launching channels extending in a longitudinal direction between a proximal end and a distal end thereof, each launching channel being configured for holding one of the plurality of filaments moveably arranged therein; and
a steering tip affixed to a distal end thereof of at least one of the plurality of filaments, wherein the a steering tip comprises a portion tapering in a longitudinal direction of the at least one of the plurality of filaments thereby narrowing toward a distal end of the steering tip, the tapered portion being rotationally asymmetrical about a longitudinal axis of the at least one of the plurality of filaments and configured for guiding the at least one of the plurality of filaments along a pre-set trajectory; and
at least two types of a cranial anchor, each type of the at least two types of the cranial anchor being configured to be secured to a skull of a subject,
the first type of cranial anchor comprising:
a proximal end forming an outer flange;
an elongated distal end for inserting into a skull aperture, wherein an axial lumen is provided, the axial lumen being tapered in a longitudinal direction of the cranial anchor and narrowing toward the distal end;
wherein the proximal end comprises at least one groove extending from a circumference of the outer flange toward a central axis of the cranial anchor, the at least one groove is configured for aligning, at the distal end of the cranial anchor, with at least one of the plurality of launching channels of the brain invasive launcher and for receiving and guiding the at least one of the plurality of filaments into the least one of the plurality of launching channels, and wherein the axial lumen is configured for receiving and guiding the brain invasive launcher, and wherein the axial lumen provides a pivot point for directing the brain invasive launcher; and
the second type of cranial anchor comprising:
a proximal end forming an outer flange;
an elongated distal end for inserting into a skull aperture, wherein an axial lumen is provided, the axial lumen being tapered in a longitudinal direction of the cranial anchor and narrowing toward the distal end;
wherein the proximal end comprises at least one groove extending from a circumference of the outer flange toward a central axis of the cranial anchor, the at least one groove is configured for aligning, at the distal end of the cranial anchor, with at least one of the plurality of launching channels of the brain invasive launcher and for receiving and guiding the at least one of the plurality of filaments into the least one of the plurality of launching channels, and wherein the axial lumen is configured for receiving and guiding the brain invasive launcher,
wherein the kit of parts comprises at least two types of the plurality of filaments, and at least two types of the steering tips.

15. The kit according to claim 14, wherein the distal end of the steering tip is offset from the longitudinal axis of the at least one of the plurality of filaments.

16. The kit according to claim 14, wherein the brain invasive launcher comprises a launcher position indicator configured to determine a location of the brain invasive launcher in a brain of a subject.

17. The kit according to claim 14, wherein the at least one of the plurality of filaments is configured to be in an installation state, in which the filament is housed in the launching channel, and a working state, in which the filament is extended beyond the distal end of the brain invasive launcher when the same is in a fixed position.

18. The kit according to claim 14, wherein the at least one of the plurality of filaments comprises a plurality of apertures.

19. The kit according to claim 14, wherein the steering tip comprises a steering tip position indicator configured to determine a location of the steering tip, a location of the at least one of the plurality of filaments, or both in a brain of a subject.

20. The kit according to claim 14, wherein the at least one of the plurality of filaments is configured to collect measurement data.

21. The kit according to claim 20, wherein the at least one of the plurality of filaments is an optical fiber.

22. The kit according to claim 20, wherein the at least one of the plurality of filaments is an electrical wire.

23. The kit according to claim 14, further comprising a multi-lumen stylet connected to the brain invasive launcher, wherein the multi-lumen stylet comprises a plurality of channels configured for holding the plurality of filaments, and wherein the plurality of channels is aligned with the plurality of launching channels of the brain invasive launcher.

24. The kit according to claim 14, wherein the brain interaction apparatus further comprises a multi-lumen stylet connected to the brain invasive launcher, wherein the multi-lumen stylet comprises a plurality of channels configured for holding the plurality of filaments, and wherein the plurality of channels is aligned with the plurality of launching channels of the brain invasive launcher, and wherein the elongated distal end is provided with a narrowed section having a diameter adjusted to a diameter of the multi-lumen stylet such that the plurality of filaments is brought into the channels.

25. The kit according to claim 24, wherein the narrowed section provides a pivotal point for the multi-lumen stylet.

26. A method comprising providing a brain interaction apparatus comprising:
   a plurality of filaments;
   a brain invasive launcher having a plurality of launching channels extending in a longitudinal direction between a proximal end and a distal end thereof, each launching channel being configured for holding one of the plurality of filaments moveably arranged therein; and
   a steering tip affixed to a distal end thereof of at least one of the plurality of filaments, wherein the steering tip comprises a portion tapering in a longitudinal direction of the at least one of the plurality of filaments thereby narrowing toward a distal end of the steering tip, the tapered portion being rotationally asymmetrical about a longitudinal axis of the at least one of the plurality of filaments and configured for guiding the at least one of the plurality of filaments along a pre-set trajectory;
   providing a cranial anchor inserted in a skull of a subject, the cranial anchor being configured to be secured to a skull of a subject, the cranial anchor comprising a proximal end forming an outer flange; an elongated distal end for inserting into a skull aperture, wherein an axial lumen is provided, the axial lumen being tapered in a longitudinal direction of the cranial anchor and narrowing toward the distal end; wherein the proximal end comprises at least one groove extending from the circumference of the outer flange toward a central axis of the cranial anchor, the at least one groove is configured for aligning, at the distal end of the cranial anchor, with at least one of the plurality of launching channels of the brain invasive launcher and for receiving and guiding the at least one of the plurality of filaments into the least one of the plurality of launching channels, and wherein the axial lumen is configured for receiving and guiding the brain invasive launcher, and wherein the axial lumen provides a pivot point for directing the brain invasive launcher;
   connecting the brain invasive launcher to the cranial anchor, thereby having at least the brain invasive launcher entering the brain of the subject; and
   feeding at least one of the plurality of filaments beyond the distal end of the brain invasive launcher in a trajectory in relation to the brain invasive launcher while the brain invasive launcher remains in a fixed position, thereby reaching a pre-determined location of the brain.

27. The method according to claim 26, wherein extending at least one of the plurality of filaments comprises rotating the at least one of the plurality of filaments along its longitudinal axis in order to adjust the trajectory and arrive at the pre-determined location.

28. The method according to claim 26, further comprising
   collecting data, collecting biological material, or both associated with the pre-determined location via the at least one of the plurality of filaments; and
   analyzing the collected data, the collected biological material, or both in order to determine at least one of a setup of the collection of biological material, a setup of the collection of data, and a setup of an injection of at least one substance.

29. The method according to claim 28, wherein the step of collecting data, collecting biological material, or both is performed during a collection phase being at least 24 hours.

30. The method according to claim 26, further comprising injecting at least one substance into the brain at one or more injecting locations via the at least one of the plurality of filaments.

31. The method according to claim 30, wherein the step of injecting at least one substance is performed during an injection phase being at least 24 hours.

32. The method according to claim 26, further comprising filling an upper portion of the axial lumen with an inert, resilient material in order to seal the brain interaction apparatus from an external environment.

\* \* \* \* \*